United States Patent [19]
Sagane et al.

[11] Patent Number: 6,153,767
[45] Date of Patent: Nov. 28, 2000

[54] PRODUCTION PROCESS FOR PYROMELLITIC DIANHYDRIDE

[75] Inventors: Toshio Sagane; Tsukasa Takahashi, both of Himeji; Yasuhisa Emoto, Hyogo-ken, all of Japan

[73] Assignee: Nippon Shokubai Co Ltd, Osaka, Japan

[21] Appl. No.: 09/270,742

[22] Filed: Mar. 16, 1999

[30] Foreign Application Priority Data

Mar. 17, 1998 [JP] Japan ................................. 10-065982

[51] Int. Cl.$^7$ ................................................ C07D 493/04
[52] U.S. Cl. .......................................................... 549/239
[58] Field of Search ............................................. 549/239

[56] References Cited

U.S. PATENT DOCUMENTS

| | | | |
|---|---|---|---|
| 3,507,813 | 4/1970 | Vrbaski et al. | 549/239 |
| 4,146,734 | 3/1979 | Slinkard | 562/548 |
| 4,665,200 | 5/1987 | Nakanishi et al. | 549/239 |
| 5,504,218 | 4/1996 | Takahashi et al. | 549/239 |

FOREIGN PATENT DOCUMENTS

| | | |
|---|---|---|
| 0163231A | 4/1985 | European Pat. Off. . |
| 0405508A | 1/1991 | European Pat. Off. . |

OTHER PUBLICATIONS

Derwent Publications Ltd., London, GB; AN 1997–364357, Sep. 27, 1995 Section CH, Week 199734 (Abstract).
Derwent Publications Ltd., London, GB; AN 1986–084433, Feb. 12, 1986 Section CH, Week 198613 (Abstract).
Derwent Publications Ltd., London, GB; AN 1974–67211V, Aug. 27, 1974 Section CH, Week 197438 (Abstract).

*Primary Examiner*—Bernard Dentz

[57] ABSTRACT

Provided is a process for producing pyromellitic dianhydride by feeding 1,2,4,5-tetraalkylbenzene to a fixed bed multitubular type reactor charged with a catalyst layer to carry out catalytic vapor phase oxidation. This process is characterized by dividing the catalyst layer into at least two layers to charge a layer at an outlet side of reaction gas and a layer at an inlet side of raw material mixed gas with the following catalyst A and catalyst B respectively or dividing the catalyst layer into at least three layers to charge a layer at an outlet side of reaction gas, an intermediate layer and a layer at an inlet side of raw material mixed gas with the following catalyst A, catalyst B and catalyst C respectively:

- catalyst A: a catalyst containing $V_a(A)_bP_cAg_d(B)_eO_x$, wherein (A) represents at least one element selected from Mo and W; (B) represents at least one element selected from alkaline metals and alkaline earth metals; a to e each represent an atomic number thereof,

- catalyst B: a catalyst containing $V_aTi_b(C)_c(D)_dCe_eO_x$ wherein (C) represents at least one element selected from rare earth elements (excluding cerium); (D) represents at least one element selected from P, Sb, Hf, Nb, T, B and S; a to e and x each represent an atomic number thereof, and

- catalyst C: a catalyst containing $V_a(E)_b(F)_c(G)_dO_x$, wherein (E) represents at least one element selected from alkaline metals; (F) represents at least one element selected from P and Cu; (G) represents at least one element selected from silver, sulfur, tantalum, boron, tungusten, and molybdenum; a to d and x each represent an atomic number thereof.

8 Claims, 1 Drawing Sheet

PRODUCTION PROCESS FOR PYROMELLITIC DIANHYDRIDE

The present invention relates to a production process for pyromellitic dianhydride. More specifically, the present invention relates to a process for producing high purity pyromellitic dianhydride at a high yield by subjecting 1,2,4,5-tetraalkylbenzene to catalytic vapor phase oxidation.

It is widely carried out in an industrial scale to subject 1,2,4,5-tetraalkylbenzene to catalytic vapor phase oxidation to produce pyromellitic dianhydride. Many patents are filed on catalysts and reaction processes used for this catalytic vapor phase oxidation.

It is publicly known as well to carry out catalytic vapor phase oxidation using a catalyst layer divided into two or more layers. Methods in which hot spots are inhibited from being produced in a catalyst layer by using plural catalyst layers having different activities are disclosed in European Patent 163,231 and Japanese Patent Application Laid-Open No. 245857/1989.

Further, it is described in U.S. Pat. No. 5,504,218 that tetraalkylbenzene is subjected to vapor phase oxidation by dividing a catalyst layer into two or more layers to provide a layer of a catalyst containing vanadium and molybdenum and/or tungsten [Mo (W)/V (atomic ratio)=0.01 to 2] at an outlet side of reaction gas and a layer of a catalyst containing vanadium and molybdenum and/or tungsten [Mo (W)/V (atomic ratio)<0.01] or a layer of a catalyst containing vanadium and alkaline metal [alkaline metal/V (atomic ratio)=0.1 to 2.5] at an inlet side of raw material gas.

The foregoing process described in U.S. Pat. No. 5,504,218 has achieved in its own way an object of producing high purity pyromellitic dianhydride at a high yield, but it is industrially desirable to achieve a higher yield of pyromellitic dianhydride.

Thus, an object of the present invention is to provide a process for producing high purity pyromellitic dianhydride at a high yield by subjecting 1,2,4,5-tetraalkylbenzene to catalytic vapor phase oxidation.

The present invention intends to achieve the object described above by using a novel catalyst in place of "the second catalyst (B)" disposed before the first "catalyst (A)" in the process described in U.S. Pat. No. 5,504,218.

According to the present invention, provided is a process for producing pyromellitic dianhydride by feeding raw material mixed gas containing 1,2,4,5-tetraalkylbenzene and molecular oxygen to a fixed bed multitubular type reactor charged with a catalyst layer to carry out catalytic vapor phase oxidation, wherein the catalyst layer is divided into at least two layers, and a layer at an outlet side of reaction gas and a layer at an inlet side of raw material mixed gas are charged with the following catalyst A and catalyst B respectively.

Catalyst A

A catalyst represented by the following formula (1):

$$V_a(A)_bP_cAg_d(B)_eO_x \quad (1)$$

wherein V represents vanadium; P represents phosphorus; Ag represents silver; (A) represents at least one element selected from molybdenum and tungsten; (B) represents at least one element selected from alkaline metal and alkaline earth metals; O represents an oxygen element; a, b, c, d, e and x each represent an atomic number thereof, and when a is 1, $0<b\leq 2$, $0<c\leq 1$, d=0 to 0.2 and e=0 to 0.1, and x is a value determined by oxidation states of the respective elements other than an oxygen element.

Catalyst B

A catalyst represented by the following formula (2):

$$V_aTi_b(C)_c(D)_dCe_eO_x \quad (2)$$

wherein V represents vanadium; Ti represents titanium; Ce represents cerium; (C) represents at least one element selected from rare earth elements (excluding cerium); (D) represents at least one element selected from phosphorus, antimony, hafnium, niobium, tantalum, boron and sulfur; O represents an oxygen element; a, b, c, d, e and x each represent an atomic number thereof, and when a is 1, $0<b\leq 500$, $0<c\leq 0.5$, d=0 to 1 and e=0 to 0.5, and x is a value determined by oxidation states of the respective elements other than an oxygen element.

Further, according to the present invention, provided is a process for producing pyromellitic dianhydride by feeding raw material mixed gas containing 1,2,4,5-tetraalkylbenzene and molecular oxygen to a fixed bed multitubular type reactor charged with a catalyst layer to carry out catalytic vapor phase oxidation, wherein the catalyst layer is divided into at least three layers, and a layer at an outlet side of reaction gas, an intermediate layer and a layer at an inlet side of raw material mixed gas are charged with the following catalyst A, catalyst B and catalyst C respectively.

Catalyst A
  Same as described above.
Catalyst B
  Same as described above.
Catalyst C A catalyst represented by the following formula (3):

$$V_a(E)_b(F)_c(G)_dO_x \quad (3)$$

wherein V represents vanadium; (E) represents at least one element selected from alkaline metals; (F) represents at least one element selected from phosphorus and copper; (G) represents at least one element selected from silver, sulfur, tantalum, boron, tungusten, and molybdenum; O represents an oxygen element; a, b, c, d and x each represent an atomic number thereof, and when a is 1, $0<b\leq 2.5$, c=0 to 3 and d=0–2, and x is a value determined by oxidation states of the respective elements other than an oxygen element.

In the attached drawings.

In the respective drawings, the left side is an inlet side of raw material mixed gas, and the right side is an outlet side of reaction gas.

Figure 1:
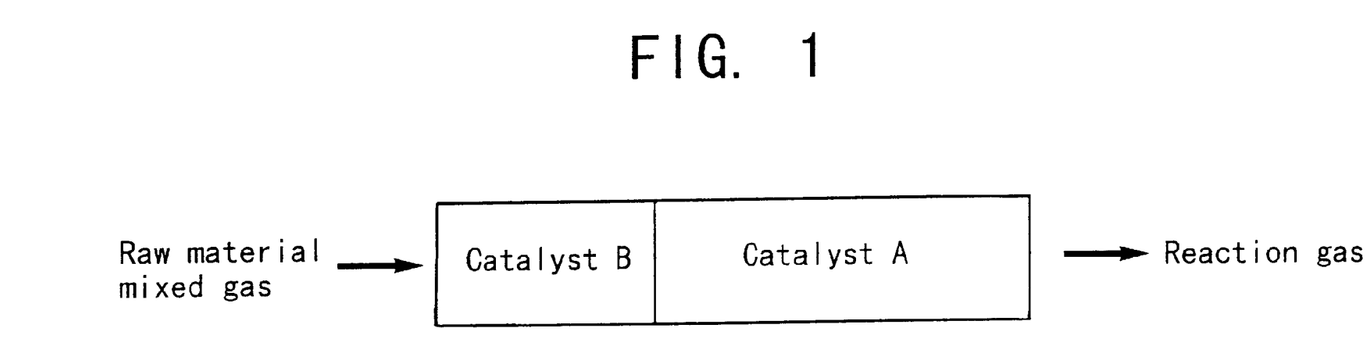
FIG. 1 is a block drawing showing the kinds of catalysts with which the respective catalyst layers are charged when a catalyst layer is divided into 12 layers.

First, an embodiment shown in FIG. 1, that is, the case where the catalyst layer is divided into 2 layers shall be explained. In this case, the layer at the outlet side of the reaction gas is charged with the catalyst A, and the layer at the inlet side of the raw material mixed gas is charged with the catalyst B. The present invention is characterized by using a novel catalyst as the catalyst B.

The catalyst A is represented by the following formula (1):

$$V_a(A)_bP_cAg_d(B)_eO_x \quad (1)$$

wherein V represents vanadium; P represents phosphorus; Ag represents silver; (A) represents at least one element selected from molybdenum and tungsten; (B) represents at least one element selected from alkaline metals and alkaline earth metals; O represents an oxygen element; a, b, c, d, e and x each represent an atomic number thereof, and when a is 1, $0<b\leq2$, $0<c\leq1$, d=0 to 0.2 and e=0 to 0.1, and x is a value determined by oxidation states of the respective elements other than an oxygen element.

In the catalyst A, at least one element (hereinafter referred to as [molybdenum and/or tungsten]) selected from molybdenum and tungsten has a content of exceeding 0 and 2 or less, preferably 0.01 to 2 and more preferably 0.05 to 1 in terms of an atomic ratio based on vanadium. The content of molybdenum and/or tungsten falling in this range raises a selectivity from an intermediate oxide such as dimethyl phthalate and aldehydes to pyromellitic dianhydride and can inhibit resulting pyromellitic dianhydride from being oxidized again.

Phosphorus has a content of exceeding 0 and 1 or less, preferably 0.002 to 1 and more preferably 0.01 to 1 in terms of an atomic ratio based on vanadium. The content of phosphorus falling in this range elevates the yield of pyromellitic dianhydride.

The catalyst A may contain silver as an optional component in a proportion of 0.2 or less, preferably 0.001 to 0.2 and more preferably 0.01 to 0.1 in terms of an atomic ratio based on vanadium. Further, it may contain at least one selected from alkaline metals and alkaline earth metals in a proportion of 0.1 or less, preferably 0.001 to 0.1 and more preferably 0.001 to 0.05 in terms of an atomic ratio based on vanadium. Use of them raises the yield of pyromellitic dianhydride.

The production method of the catalyst A shall not specifically be restricted, and the catalyst can be prepared by using nitrates, carbonates, organic acid salts, ammonium salts and oxides each containing the respective elements according to methods usually used for preparing this kind of catalysts.

The catalyst A is used usually carrying the components on a carrier. Any carriers can be used as long as they are inert carriers usually used. Suitably used are, for example, inorganic porous carriers having an apparent porosity of 5 to 50% and a BET specific surface area of 5 $m^2/g$ or less, preferably 0.05 to 1 $m^2/g$. Among them, suitably used is self-sintered type silicon carbide having an aluminum content of 10% by weight or less, preferably 3% by weight or less and an Si content of 50% by weight or more, preferably 90% or more and particularly about 98%. The shape of the carrier shall not specifically be restricted, and any shapes of sphere, ring, cylinder, cone and saddle may be used. The size thereof shall not specifically be restricted, and in the case of, for example, sphere, those having an average particle diameter of 3 to 15 mm, preferably 3 to 10 mm are used.

The components can be carried on the carrier by conventionally known methods such as a spray deposition method and an impregnation deposition method. For example, a carrier heated to 90 to 350° C., preferably 200 to 350° C. is sprayed with an aqueous solution or a slurry obtained by adding nitrate, carbonate, organic acid salt, ammonium salt and oxide of vanadium, molybdenum and/or tungsten and phosphorus to water and homogeneously mixing them to carry them thereon and then calcined at a temperature of 300 to 650° C., preferably 400 to 600° C. for 1 to 10 hours, preferably 2 to 6 hours. The total carrying amount (in terms of an amount reduced to oxide) of vanadium, molybdenum and/or tungsten and phosphorus is usually 3 to 100 g, preferably 5 to 30 g per an apparent volume of 100 cc of the carrier.

In preparing the catalyst A, titanium oxide, tin oxide and zirconium oxide can be used as a powder for dispersing the catalyst active ingredients. In particular, those having a BET specific surface area of 5 to 100 $m^2/g$, preferably 5 to 40 $m^2/g$ are used. The catalyst active ingredients can be inhibited from separating from the carrier by using them. Further, in order to raise the catalyst strength, fibrous matters such as silicon carbide (SiC) whisker may be added to a slurry containing the catalyst active ingredients in preparing the catalyst and mixed well, and then it may be carried on the carrier.

The catalyst A with which the layer at the outlet side of reaction gas is charged does not necessarily have to be the same, and the kind of the elements and the atomic ratio thereof can suitably be changed as long as they fall in the ranges of the element composition represented by the formula (1) described above. To be specific, the atomic ratio of molybdenum and/or tungsten based on vanadium may be changed continuously or intermittently from the inlet side to the outlet side. For the purpose of reducing the maximum temperature of the catalyst layer, the catalyst may suitably be diluted with inactive materials usually used for dilution, for example, silica, alumina, steatite, cordierite, mullite, silicon carbide and metal Raschig rings.

The catalyst A has the characteristic that the oxidation activity to resulting pyromellitic dianhydride is low and the selectivity from an intermediate oxide to pyromellitic dianhydride is high. This makes it suitable as a catalyst charged into the layer at the outlet side of reaction gas. The catalyst A is described in U.S. Pat. No. 5,504,218, and detailed action and effect thereof can be referred to this publication.

The catalyst B is represented by the following formula (2):

$$V_aTi_b(C)_c(D)_dCe_eO_x \qquad (2)$$

wherein V represents vanadium; Ti represents titanium; (C) represents at least one element selected from rare earth elements (excluding cerium); (D) represents at least one element selected from phosphorus, antimony, hafnium, niobium, tantalum, boron and sulfur; O represents an oxygen element; a, b, c, d, e and x each represent an atomic number thereof, and when a is 1, $0<b\leq500$, $0<c\leq0.5$, d=0 to 1 and e=0 to 0.5, and x is a value determined by oxidation states of the respective elements other than an oxygen element.

In the catalyst B, titanium has a content of exceeding 0 to 500 or less, preferably 2 to 500, more preferably 1 to 200 and particularly preferably 2 to 50 in terms of an atomic ratio based on vanadium. The content of titanium falling in this range can raise the yield of pyromellitic dianhydride and inhibit combustion gas from being produced.

Typical examples of rare earth elements (excluding cerium) include scandium, yttrium, lanthanum, praseodymium, neodymium, samarium, europium, gadolinium, terbium, dysprosium, holmium, erbium, thulium, ytterbium and lutetium. The rare earth elements have a content of exceeding 0 to 0.5 or less, preferably 0.0005 to 0.5 and more preferably 0.001 to 0.2 in terms of an atomic ratio based on vanadium. The content of the rare earth elements falling in this range can raise the yield of pyromellitic dianhydride.

The catalyst B may contain at least one element selected from phosphorus, antimony, hafnium, niobium, tantalum, boron and sulfur as an optional component in a proportion of 1 or less, preferably 0.001 to 1 and more preferably 0.001 to 0.5 in terms of an atomic ratio based on vanadium. Further, the catalyst may contain cerium in a proportion of 0.5 or less, preferably 0.0005 to 0.5 and more preferably 0.001 to 0.2 in terms of an atomic ratio based on vanadium. Use of them can elevate the yield of pyromellitic dianhydride.

The production method of the catalyst B shall not specifically be restricted, and the catalyst can be prepared by using nitrates, carbonates, organic acid salts, ammonium salts and oxides each containing the respective elements according to methods usually used for preparing this kind of catalysts.

The catalyst B is used usually carrying the components on a carrier. Any carriers can be used as long as they are inert carriers usually used. Suitably used are, for example, inorganic porous carriers having an apparent porosity of 5 to 50% and a BET specific surface area of 5 m²/g or less, preferably 0.05 to 1 m²/g. Among them, suitably used is self-sintered type silicon carbide having an aluminum content of 10% by weight or less, preferably 3% by weight or less and an Si content of 50% by weight or more, preferably 90% or more and particularly about 98%. The shape of the carrier shall not specifically be restricted, and any shapes of sphere, ring, cylinder, cone and saddle may be used. The size thereof shall not specifically be restricted as well, and in the case of, for example, sphere, those having an average particle diameter of 3 to 15 mm, preferably 3 to 10 mm are used.

The components can be carried on the carrier by conventionally known methods such as a spray deposition method and an impregnation deposition method. For example, a carrier heated to 90 to 350° C., preferably 200 to 350° C. is sprayed with an aqueous solution or a slurry obtained by adding nitrate, carbonate, organic acid salt, ammonium salt and oxide of vanadium, titanium and rare earth elements to water and homogeneously mixing them to carry them thereon and then can be calcined at a temperature of 300 to 650° C., preferably 400 to 600° C. for 1 to 10 hours, preferably 2 to 6 hours. The total carrying amount (in terms of an amount reduced to oxide) of vanadium, titanium and rare earth elements is usually 3 to 100 g, preferably 5 to 30 g per an apparent volume of 100 cc of the carrier.

In preparing the catalyst B, tin oxide and zirconium oxide can be used as a powder for dispersing the catalyst active ingredients. In particular, those having a BET specific surface area of 5 to 100 m²/g, preferably 5 to 40 m²/g are preferably used. Use of them can inhibit the catalyst active ingredients from separating from the carrier. Further, in order to raise the catalyst strength, fibrous matters such as silicon carbide (SiC) whisker may be added to a slurry containing the catalyst active ingredients in preparing the catalyst and mixed well, and then it can be carried on the carrier.

The catalyst B with which the layer at the inlet side of reaction gas is charged does not necessarily have to be the same, and the kind of the elements and the atomic ratio thereof can suitably be changed as long as they fall in the ranges of the element composition represented by the formula (2) described above. To be specific, the atomic ratio of a rare earth element based on vanadium may be changed continuously or intermittently from the inlet side to the outlet side. For the purpose of reducing the maximum temperature of the catalyst layer, the catalyst may suitably be diluted with inactive materials usually used for dilution, for example, silica, alumina, steatite, cordierite, silicon carbide and metal Raschig rings.

The catalyst B has a high oxidation activity to 1,2,4,5-tetraalkylbenzene and is excellent particularly in a low temperature activity. This makes it suitable as a catalyst charged into the layer at the inlet side of reaction gas.

A layer length ratio of a catalyst layer (hereinafter referred to as [catalyst A layer] charged with the catalyst A to a catalyst layer (hereinafter referred to as [catalyst B layer] charged with the catalyst B shall not specifically be restricted but usually, the catalyst A layer is preferably longer than the catalyst B layer. To be specific, the length of the catalyst A layer/the length of the catalyst B layer can be set to 10/1 to 1/1, preferably 8/1 to 2/1. When an inactive material for dilution in addition to the catalyst is charged, the layer length is defined by the substantial layer length excluding the inactive material for dilution.

The amounts of the catalyst A and the catalyst B charged into the respective reactors are varied according to the catalyst performances and therefore properly adjusted to the suitable amounts and charged. Usually, the charging amount of the catalyst A can be set so that a space velocity in this catalyst layer is 2,000 to 20,000 hr⁻¹, preferably 3,000 to 15,000 hr⁻¹. The charging amount of the catalyst B can usually be set so that a space velocity in this catalyst layer is 10,000 to 50,000 hr⁻¹, preferably 15,000 to 40,000 hr⁻¹. When the catalyst layer is diluted, a space velocity thereof has to be lower than when it is not diluted and is reduced to the range described above or less in a certain case depending on the degree of dilution.

In an embodiment shown in FIG. 1, stain from the catalyst having a different composition can be prevented by providing a layer of an inactive material, for example, silica, alumina, steatite, cordierite, silicon carbide or metal Raschig rings in the middle between the catalyst A layer and the catalyst B layer.

Figure 2:
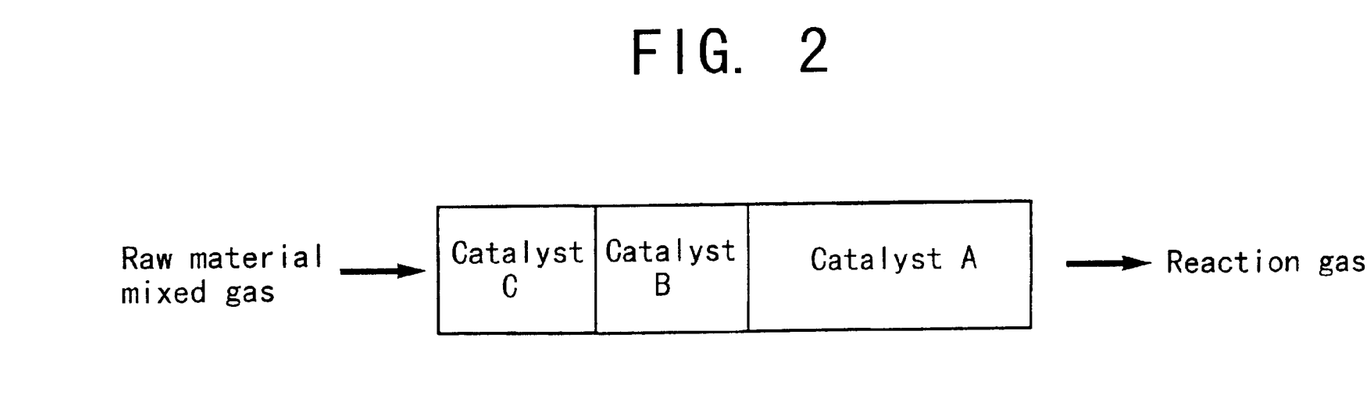
FIG. 2 is a block drawing showing the kinds of catalysts with which the respective catalyst layers are charged when a catalyst layer is divided into 3 layers.

Next, an embodiment shown in FIG. 2, that is, the case where the catalyst layer is divided into 3 layers shall be explained. In this case, charged are a layer at the outlet side of reaction gas with the catalyst A, a layer at the inlet side of reaction gas with the catalyst C and a layer in the middle between them with the catalyst B. The catalyst A and the catalyst B are the same as those described above. The present invention is characterized by using a novel catalyst as the catalyst B similarly to the case of dividing into two layers described above.

The catalyst C is represented by the following formula (3):

$$V_a(E)_b(F)_c(G)_d O_x \qquad (3)$$

wherein V represents vanadium; (E) represents at least one element selected from alkaline metals; (F) represents at least one element selected from phosphorus and copper; (G) represents at least one element selected from silver, sulfur, tantalum, boron, tungusten, and molybdenum; O represents an oxygen element; a, b, c, d and x each represent an atomic number thereof, and when a is 1, $0 < b \leq 2.5$, $c = 0$ to 3 and $d = 0-2$, and x is a value determined by oxidation states of the respective elements other than an oxygen element.

In the catalyst C, at least one element selected from alkaline metals has a content of exceeding 0 to 2.5 or less, preferably 0.1 to 2.5 and more preferably 0.2 to 2 in terms of an atomic ratio based on vanadium. The content of the alkaline metals falling in this range can raise the yield of pyromellitic acid.

The catalyst C may contain at least one element selected from phosphorus and copper as an optional component in a proportion of 3 or less, preferably 0.2 to 3 and more preferably 0.2 to 2.5 in terms of an atomic ratio based on vanadium. The yield of pyromellitic dianhydride can be elevated by using this.

The production method of the catalyst B shall not specifically be restricted, and the catalyst can be prepared by using nitrates, carbonates, organic acid salts, ammonium salts and oxides each containing the respective elements according to methods usually used for preparing this kind of catalysts.

In the catalyst C, inorganic powder is preferably added for the purpose of dispersing the catalyst active materials. Inactive powders are preferred as this inorganic powder and include, for example, thermally stable inorganic powders containing silicon, to be specific, natural minerals such as crystalline silica, amorphous silica, silicon carbide, mullite, cordierite and diatomaceous earth. Among them, inexpensive natural minerals such as diatomaceous earth are suitably used. Addition of these inorganic powders makes it possible to suitably raise the activity of the catalyst without reducing the selectivity to further elevate the effect as a catalyst charged at the inlet side of reaction gas. The addition amount of these inorganic powders are varied according to a particle size distribution, a particle form and a specific surface area and therefore can not absolutely be specified. The catalyst active ingredients covers preferably the whole surface of the inorganic powders, and usually, they are added in 0.05 to 10 times by weight, particularly 0.1 to 5 times by weight as much amount as the catalyst active ingredients (in terms of an amount converted to oxide). Inorganic powders such as titania which has so far been used for conventional catalysts for producing pyromellitic acid has an action to raise the activity of vanadium, and this reduces the selectivity of the catalyst C. Accordingly, it is not preferred to add such compound in a large quantity for the purpose of dispersing the catalyst active ingredients.

The catalyst C is usually used carrying the components on a carrier. Any carriers can be used as long as they are inert carriers usually used. Suitably used are, for example, inorganic porous carriers having an apparent porosity of 5 to 50% and a BET specific surface area of 5 $m^2/g$ or less, preferably 0.05 to 1 $m^2/g$. Among them, suitably used is self-sintered type silicon carbide having an aluminum content of 10% by weight or less, preferably 3% by weight or less and an Si content of 50% by weight or more, preferably 90% or more and particularly about 98%. The shape of the carrier shall not specifically be restricted, and any shapes of sphere, ring, cone and saddle may be used. The size thereof shall not specifically be restricted, and in the case of, for example, sphere, those having an average particle diameter of 3 to 15 mm, preferably 3 to 10 mm are used.

The components can be carried on the carrier by conventionally known methods such as a spray deposition method and an impregnation deposition method. For example, a carrier heated to 90 to 350° C., preferably 200 to 350° C. is sprayed with an aqueous solution or a slurry obtained by adding inorganic salts such as nitrates of vanadium and alkaline metals, or organic acid salts such as carbonates and ammonium salts to water and homogeneously mixing them to carry them thereon and then can be calcined at a temperature of 400 to 700° C., preferably 500 to 650° C. for 1 to 10 hours, preferably 2 to 6 hours. The total carrying amount (in terms of an amount reduced to oxide) of vanadium and alkaline metals is usually 3 to 100 g, preferably 10 to 70 g per an apparent volume of 100 cc of the carrier.

In the production method for the catalyst C, these respective elements are preferably mixed as homogeneously as possible, and the catalyst C is prepared by stirring, mixing or kneading a starting material containing the elements described above in a solvent such as water to prepare a liquid or a slurry and carrying this on a carrier. Further, in order to raise the catalyst strength, fibrous matters such as silicon carbide (SiC) whisker may be added to the slurry containing the catalyst active ingredients in preparing the catalyst and mixed well, and then it may be carried on the carrier.

The catalyst C charged into the layer at the inlet side of reaction gas does not necessarily have to be the same, and the kind of the elements and the atomic ratio thereof can suitably be changed as long as they fall in the ranges of the element composition represented by the formula (3) described above. To be specific, the atomic ratio of the alkaline metal based on vanadium may be changed continuously or intermittently from the inlet side to the outlet side.

The catalyst C is described in U.S. Pat. No. 5,504,218, and detailed action and effect thereof can be referred to this patent.

The length of a layer (hereinafter referred to as [catalyst C layer] charged with the catalyst C shall not specifically be restricted and can be ⅕ or more of the length of the catalyst A layer. Usually, it can be ⅕ to ½ of the length of the catalyst A layer.

The amounts of the catalyst A, the catalyst B and the catalyst C charged into the respective reactors are varied according to the catalyst performances and therefore properly adjusted to the suitable amounts and charged. Usually, the charging amount of the catalyst A can be set so that a space velocity in this catalyst layer is 2,000 to 20,000 $hr^{-1}$, preferably 3,000 to 15,000 $hr^{-1}$. The charging amount of the catalyst B can usually be set so that a space velocity in this catalyst layer is 10,000 to 50,000 $hr^{-1}$, preferably 15,000 to 40,000 $hr^{-1}$. Further, the charging amount of the catalyst C can usually be set so that a space velocity in this catalyst layer is 5,000 to 50,000 $hr^{-1}$, preferably 10,000 to 30,000 $hr^{-1}$. When the catalyst layer is diluted, a space velocity thereof has to be lower than when it is not diluted and is reduced to the range described above or less in a certain case depending on the degree of dilution.

In an embodiment shown in FIG. 2, stain from the catalysts having a different composition can be prevented by providing a layer of an inactive material, for example, silica, alumina, steatite, cordierite, silicon carbide or metal Raschig rings in the middle between the catalyst A layer and the catalyst B layer and/or between the catalyst B layer and the catalyst C layer.

Conditions in carrying out the present invention shall not specifically be restricted, and it can be carried out under conditions usually used for this kind of reactions. For example, a reactor having a minor diameter of 15 to 40 mm, preferably 15 to 30 mm is used. The reaction temperature is 340 to 460° C., preferably 360 to 440° C. in terms of a temperature of a heat transfer medium. The space velocities are as described above, but the space velocity in the whole catalyst system is set to 1,000 to 15,000 $hr^{-1}$, preferably 3,000 to 10,000 $hr^{-1}$.

Durene can be given as a typical example of 1,2,4,5-tetraalkylbenzene used as a raw material in the present invention. The concentration of 1,2,4,5-tetraalkylbenzene contained in raw material gas shall not specifically be restricted but is usually 10 to 100 $g/Nm^3$, preferably 20 to 50 $g/Nm^3$. Molecular oxygen is used in an amount sufficient for producing pyromellitic dianhydride from 1,2,4,5-tetraalkylbenzene. Usually, air is used.

The present invention shall be explained below in further detail with reference to examples. Catalysts used here were prepared in the following manners.

Catalyst A1

Oxalic acid of 150 g was dissolved in deionized water of 200 ml, and ammonium metavanadate of 120 g and ammonium molybdate of 54.3 g were added thereto to mix them homogeneously. Then, ammonium primary phosphate of 5.9 g was dissolved therein, and deionized water was added to prepare a chemical solution of about 600 ml. A spherical self-sintered type silicon carbide carrier of 200 cc having an average particle diameter of 4 mm was put in an externally heating type rotary furnace and pre-heated to 200 to 350° C. This was sprayed with the catalyst component slurry described above to carry thereon a catalyst material of 20 g. Then, it was calcined in a kiln at 500° C. for 6 hours to thereby obtain a catalyst A1.

Catalyst A2

Oxalic acid of 150 g was dissolved in deionized water of 200 ml, and ammonium metavanadate of 120 g and ammonium molybdate of 54.3 g were added thereto to mix them homogeneously. Then, ammonium primary phosphate of 5.9 g was dissolved therein. Silver nitrate of 5.2 g which had been dissolve in advance in a small amount of deionized water was added thereto and stirred. Further, calcium nitrate tetrahydrate of 1.2 g which had been dissolve in advance in a small amount of deionized water was added thereto and stirred. Deionized water was added to prepare a chemical solution of about 600 ml. A spherical self-sintered type silicon carbide carrier of 200 cc having an average particle diameter of 4 mm was put in an externally heating type rotary furnace and pre-heated to 200 to 350° C. This was sprayed with the catalyst component slurry described above to carry thereon a catalyst material of 20 g. Then, it was calcined in a kiln at 500° C. for 6 hours to thereby obtain a catalyst A2.

The compositions (atomic ratio) of the catalyst A1 and the catalyst A2 each described above are shown in Table 1.

Catalyst B1 (comparative)

Oxalic acid of 24 g was dissolved in deionized water of 120 ml, and ammonium metavanadate of 11.7 g was added thereto. Further, titanium oxide of 80 g was added and mixed homogeneously, and deionized water was added to prepare a catalyst component slurry of about 290 ml. A spherical self-sintered type silicon carbide carrier of 200 cc having an average particle diameter of 4 mm was put in an externally heating type rotary furnace and pre-heated to 150 to 250° C. This was sprayed with the catalyst component slurry described above to carry thereon a catalyst material of 10 g. Then, it was calcined in a kiln at 550° C. for 6 hours to thereby obtain a catalyst B1 (comparative).

Catalyst B2

A catalyst B2 was prepared in the same manner as in the preparing method of the catalyst B1, except that praseodymium nitrate hexahydrate of 0.44 g was added prior to adding titanium oxide.

Catalyst B3

Oxalic acid of 24 g was dissolved in deionized water of 120 ml, and ammonium metavanadate of 11.7 g and ammonium primary phosphate of 1.7 g were added thereto and dissolved. Then, antimony trioxide of 2.19 g was added, and lanthanum nitrate hexahydrate of 0.43 g was added. Further, titanium oxide of 80 g was added and mixed homogeneously, and deionized water was added to prepare a catalyst component slurry of about 290 ml. A spherical self-sintered type silicon carbide carrier of 200 cc having an average particle diameter of 4 mm was put in an externally heating type rotary furnace and pre-heated to 150 to 250° C. This was sprayed with the catalyst component slurry described above to carry thereon a catalyst material of 10 g. Then, it was calcined in a kiln at 550° C. for 6 hours to thereby obtain a catalyst B3.

Catalyst B4

A catalyst B4 was prepared in the same manner as in the preparing method of the catalyst B3, except that praseodymium nitrate hexahydrate of 0.44 g was added in place of lanthanum nitrate hexahydrate.

Catalyst B5

A catalyst B5 was prepared in the same manner as in the preparing method of the catalyst B3, except that neodymium nitrate hexahydrate of 0.44 g was added in place of lanthanum nitrate hexahydrate.

Catalyst B6

A catalyst B6 was prepared in the same manner as in the preparing method of the catalyst B3, except that samarium nitrate hexahydrate of 0.45 g was added in place of lanthanum nitrate hexahydrate.

Catalyst B7

A catalyst B7 was prepared in the same manner as in the preparing method of the catalyst B3, except that europium nitrate hexahydrate of 0.45 g was added in place of lanthanum nitrate hexahydrate.

Catalyst B8

A catalyst B8 was prepared in the same manner as in the preparing method of the catalyst B3, except that gadolinium nitrate hexahydrate of 0.45 g was added in place of lanthanum nitrate hexahydrate.

Catalyst B9

A catalyst B9 was prepared in the same manner as in the preparing method of the catalyst B3, except that terbium nitrate hexahydrate of 0.45 g was added in place of lanthanum nitrate hexahydrate.

Catalyst B10

A catalyst B10 was prepared in the same manner as in the preparing method of the catalyst B3, except that dysprosium nitrate pentahydrate of 0.44 g was added in place of lanthanum nitrate hexahydrate.

Catalyst B11

A catalyst B11 was prepared in the same manner as in the preparing method of the catalyst B3, except that holmium nitrate hexahydrate of 0.44 g was added in place of lanthanum nitrate hexahydrate.

Catalyst B12

A catalyst B12 was prepared in the same manner as in the preparing method of the catalyst B3, except that erbium nitrate hexahydrate of 0.45 g was added in place of lanthanum nitrate hexahydrate.

Catalyst B13

A catalyst B13 was prepared in the same manner as in the preparing method of the catalyst B3, except that thulium nitrate tetrahydrate of 0.43 g was added in place of lanthanum nitrate hexahydrate.

Catalyst B14

A catalyst B14 was prepared in the same manner as in the preparing method of the catalyst B3, except that ytterbium nitrate trihydrate of 0.41 g was added in place of lanthanum nitrate hexahydrate.

Catalyst B15

A catalyst B15 was prepared in the same manner as in the preparing method of the catalyst B3, except that thulium nitrate tetrahydrate of 0.43 g in place of lanthanum nitrate hexahydrate was dissolved in deionized water of 10 ml, and 2 ml thereof was added.

Catalyst B16

A catalyst B16 was prepared in the same manner as in the preparing method of the catalyst B3, except that thulium nitrate tetrahydrate of 0.86 g was added in place of lanthanum nitrate hexahydrate.

Catalyst B17

A catalyst B17 was prepared in the same manner as in the preparing method of the catalyst B3, except that thulium nitrate tetrahydrate of 4.28 g was added in place of lanthanum nitrate hexahydrate.

Catalyst B18

Oxalic acid of 47 g was dissolved in deionized water of 120 ml, and ammonium metavanadate of 23.4 g and ammonium primary phosphate of 1.7 g were added thereto and dissolved. Then, antimony trioxide of 4.38 g was added, and thulium nitrate tetrahydrate of 0.43 g was then added. Further, titanium oxide of 80 g was added and mixed homogeneously, and deionized water was added thereto to prepare a catalyst component slurry of about 290 ml. A spherical self-sintered type silicon carbide carrier of 200 cc having an average particle diameter of 4 mm was put in an externally heating type rotary furnace and pre-heated to 150 to 250° C. This was sprayed with the catalyst component slurry described above to carry thereon a catalyst material of 10 g. Then, it was calcined in a kiln at 550° C. for 6 hours to thereby obtain a catalyst B18.

Catalyst B19

A catalyst B19 was prepared in the same manner as in the preparing method of the catalyst B3, except that praseodymium nitrate hexahydrate of 0.87 g and cerium nitrate hexahydrate of 0.43 g were added in place of lanthanum nitrate hexahydrate.

Catalyst B20

A catalyst B20 was prepared in the same manner as in the preparing method of the catalyst B3, except that holmium nitrate pentahydrate of 0.88 g and cerium nitrate hexahydrate of 0.43 g were added in place of lanthanum nitrate hexahydrate.

Catalyst B21

A catalyst B21 was prepared in the same manner as in the preparing method of the catalyst B3, except that erbium nitrate hexahydrate of 0.92 g and cerium nitrate hexahydrate of 0.43 g were added in place of lanthanum nitrate hexahydrate.

Catalyst B22

A catalyst B22 was prepared in the same manner as in the preparing method of the catalyst B3, except that thulium nitrate tetrahydrate of 0.86 g and cerium nitrate hexahydrate of 0.43 g were added in place of lanthanum nitrate hexahydrate.

Catalyst B23

Oxalic acid of 47 g was dissolved in deionized water of 120 ml, and ammonium metavanadate of 23.4 g was added thereto and dissolved. Then, antimony trioxide of 4.38 g was added, and thulium nitrate tetrahydrate of 0.43 g and niobium oxalate of 0.54 were then added. Further, titanium oxide of 80 g was added and mixed homogeneously, and deionized water was added thereto to prepare a catalyst component slurry of about 290 ml. A spherical self-sintered type silicon carbide carrier of 200 cc having an average particle diameter of 4 mm was put in an externally heating type rotary furnace and pre-heated to 150 to 250° C. This was sprayed with the catalyst component slurry described above to carry thereon a catalyst material of 10 g. Then, it was calcined in a kiln at 550° C. for 6 hours to thereby obtain a catalyst B23.

Catalyst B24

A catalyst B24 was prepared in the same manner as in the preparing method of the catalyst B23, except that hafnium oxide of 0.21 g was added in place of niobium oxalate.

Catalyst B25

A catalyst B25 was prepared in the same manner as in the preparing method of the catalyst B23, except that tantalum oxide of 0.21 g was added in place of niobium oxalate.

Catalyst B26

A catalyst B26 was prepared in the same manner as in the preparing method of the catalyst B23, except that 99.5% boric acid of 3.11 g in place of niobium oxalate was diluted with deionized water of 100 ml, and 2 ml thereof was added.

Catalyst B27

Oxalic acid of 47 g was dissolved in deionized water of 120 ml, and ammonium metavanadate of 23.4 g and ammonium primary phosphate of 1.7 g were added thereto and dissolved. Then, thulium sulfate tetrahydrate of 0.43 g was added and titanium oxide of 80 g was further added and mixed homogeneously, and deionized water was added thereto to prepare a catalyst component slurry of about 290 ml. A spherical self-sintered type silicon carbide carrier of 200 cc having an average particle diameter of 4 mm was put in an externally heating type rotary furnace and pre-heated to 150 to 250° C. This was sprayed with the catalyst component slurry described above to carry thereon a catalyst material of 10 g. Then, it was calcined in a kiln at 550° C. for 6 hours to thereby obtain a catalyst B27.

The compositions (atomic ratio) of the catalyst B1 to the catalyst B27 each described above are shown in Table 2.

Catalyst C1

Ammonium metavanadate of 93 g and 85% phosphoric acid of 46 g were added to deionized water of 450 ml to prepare a homogeneous solution. Potassium nitrate of 24.1 g, cesium nitrate of 46.5 g and copper sulfate trihydrate of 384 g were added to this solution, and diatomaceous earth (Snow Floss manufactured by Manville Co., Ltd.) of 65 g was further added and stirred well to prepare a homogeneous catalyst component slurry. Deionized water was added to adjust the whole chemical solution amount to 1400 ml. A spherical self-sintered type silicon carbide carrier of 200 cc having an average particle diameter of 4 mm was put in an externally heating type rotary furnace and pre-heated to 150 to 250° C. This was sprayed with the catalyst component slurry described above to carry thereon a catalyst material of 50 g. Then, it was calcined in a kiln at 610° C. for 6 hours to thereby obtain a catalyst C1. The composition (atomic ratio) of this catalyst C1 is shown in Table 3.

Catalyst C2

Ammonium metavanadate of 93 g was added to deionized water of 450 ml to prepare a homogeneous solution. Potassium sulfate of 20.8 g, cesium sulfate of 43.2 g and copper sulfate trihydrate of 384 g were added to the solution in this order. Further, ammonium molybdate of 14.0 g and ammonium tungustate of 21.4 g were added to the solution, and diatomaceous earth (Snow Floss manufactured by Manville Co., Ltd.) of 65 g was added and stirred well to prepare a homogeneous catalyst component slurry. Deionized water was added to adjust the whole chemical solution amount to 1400 ml. A spherical self-sintered type silicon carbide carrier of 200 cc having an average particle diameter of 4 mm was put in an externally heating type rotary furnace and pre-heated to 150 to 250° C. This was sprayed with the catalyst component slurry described above to carry thereon a catalyst material of 60 g. Then, it was calcined in a kiln at 610° C. for 6 hours to thereby obtain a catalyst C2. The composition (atomic ratio) of this catalyst C2 is shown in Table 3.

TABLE 1

| Catalyst name | Catalyst composition (atomic ratio) | | | | |
|---|---|---|---|---|---|
| | V | Mo | P | Ag | Ca |
| A1 | 100 | 30 | 5 | — | — |
| A2 | 100 | 30 | 5 | 3 | 0.5 |

TABLE 2

Catalyst composition (atomic ratio)

| Catalyst name | V | Ti | Rare earth element | Sb | P | Others |
|---|---|---|---|---|---|---|
| B1 | 10 | 100 | — | — | — | — |
| B2 | 10 | 100 | Pr (0.1) | — | — | — |
| B3 | 10 | 100 | La (0.1) | 1.5 | 1.5 | — |
| B4 | 10 | 100 | Pr (0.1) | 1.5 | 1.5 | — |
| B5 | 10 | 100 | Nd (0.1) | 1.5 | 1.5 | — |
| B6 | 10 | 100 | Sm (0.1) | 1.5 | 1.5 | — |
| B7 | 10 | 100 | Eu (0.1) | 1.5 | 1.5 | — |
| B8 | 10 | 100 | Gd (0.1) | 1.5 | 1.5 | — |
| B9 | 10 | 100 | Tb (0.1) | 1.5 | 1.5 | — |
| B10 | 10 | 100 | Dy (0.1) | 1.5 | 1.5 | — |
| B11 | 10 | 100 | Ho (0.1) | 1.5 | 1.5 | — |
| B12 | 10 | 100 | Er (0.1) | 1.5 | 1.5 | — |
| B13 | 10 | 100 | Tm (0.1) | 1.5 | 1.5 | — |
| B14 | 10 | 100 | Yb (0.1) | 1.5 | 1.5 | — |
| B15 | 10 | 100 | Tm (0.02) | 1.5 | 1.5 | — |
| B16 | 10 | 100 | Tm (0.2) | 1.5 | 1.5 | — |
| B17 | 10 | 100 | Tm (1.0) | 1.5 | 1.5 | — |
| B18 | 20 | 100 | Tm (0.1) | 3.0 | 1.5 | — |
| B19 | 10 | 100 | Pr (0.2) Ce (0.1) | 1.5 | 1.5 | — |
| B20 | 10 | 100 | Ho (0.2) Ce (0.1) | 1.5 | 1.5 | — |
| B21 | 10 | 100 | Er (0.2) Ce (0.1) | 1.5 | 1.5 | — |
| B22 | 10 | 100 | Tm (0.2) Ce (0.1) | 1.5 | 1.5 | — |
| B23 | 20 | 100 | Tm (0.1) | 3.0 | — | Nb (0.1) |
| B24 | 20 | 100 | Tm (0.1) | 3.0 | — | Hf (0.1) |
| B25 | 20 | 100 | Tm (0.1) | 3.0 | — | Ta (0.1) |
| B26 | 20 | 100 | Tm (0.1) | 3.0 | — | B (0.1) |
| B27 | 20 | 100 | Tm (0.1) | — | 1.5 | — |

TABLE 3

Catalyst composition (atomic ratio)

| Catalyst name | V | K | Cs | P | Cu | Mo | W | S |
|---|---|---|---|---|---|---|---|---|
| C1 | 1 | 0.3 | 0.3 | 0.5 | 2 | — | — | — |
| C2 | 1 | 0.3 | 0.3 | — | 2 | 0.1 | 0.1 | 0.3 |

COMPARATIVE EXAMPLE 1

A stainless steel-made reactor having a minor diameter of 20 mm and a length of 400 mm was charged with the catalyst A1 from the outlet side of reaction gas in a layer length of 150 mm. Next, it was charged with the catalyst B1 (comparative) in a layer length of 75 mm. Finally, it was charged with glass beads having an average particle diameter of 5 mm as a pre-heating layer for raw material gas in a layer length of 150 mm. Raw material mixed gas comprising durene having a concentration of 20 g/Nm$^3$ and the balance of air was passed through this catalyst layer at a rate of 3 liter/min. to carry out reaction at a space velocity of 5,400 hr$^{-1}$. The reaction temperature was controlled to an optimum temperature.

The resulting reaction gas was passed through an air cooled crystallization tube and two gas washing bottles to collect reaction products. The yield of pyromellitic acid was determined by means of liquid chromatography, and this was converted to determine the yield of pyromellitic dianhydride. The result thereof is shown in Table 4.

EXAMPLE 1

The reaction was carried out in the same manner as in Comparative Example 1, except that the catalyst B2 was substituted for the catalyst B1 (comparative). The result thereof is shown in Table 4.

EXAMPLES 2 to 26

The reaction was carried out in the same manner as in Comparative Example 1, except that the catalysts B2 to B27 were substituted for the catalyst B1 (comparative) and the catalyst A2 was substituted for the catalyst A1. The result thereof is shown in Table 4.

EXAMPLE 27

A stainless steel-made reactor having a minor diameter of 20 mm and a length of 400 mm was charged with the catalyst A1 from the outlet side of reaction gas in a layer length of 150 mm. Next, it was charged with the catalyst B12 in a layer length of 75 mm. Further, it was charged with the catalyst C1 in a layer length of 150 mm. Finally, it was charged with glass beads having an average particle diameter of 5 mm as a pre-heating layer for raw material gas in a layer length of 100 mm. Raw material mixed gas comprising durene having a concentration of 20 g/Nm$^3$ and the balance of air was passed through this catalyst layer at a rate of 6.3 liter/min. to carry out reaction at a space velocity of 4,400 hr$^{-1}$. The reaction temperature was controlled to an optimum temperature.

The resulting reaction gas was passed through an air cooled crystallization tube and two gas washing bottles to collect reaction products. The yield of pyromellitic acid was determined by means of liquid chromatography, and this was converted to determine the yield of pyromellitic dianhydride. The result thereof is shown in Table 5.

EXAMPLE 28

The reaction was carried out in the same manner as in Example 27, except that the catalyst B19 was substituted for the catalyst B12 and the catalyst C2 was substituted for the catalyst C1. The result thereof is shown in Table 5.

TABLE 4

| | Reaction gas inlet side | | Reaction gas outlet side | | Space velocity hr$^{-1}$ | Reaction temperature °C. | PMDA Yield mol % |
|---|---|---|---|---|---|---|---|
| | Catalyst | Layer length mm | Catalyst | Layer length mm | | | |
| Comparative Example 1 | B1 | 75 | A1 | 150 | 5400 | 400 | 64.3 |
| Example 1 | B2 | 75 | A1 | 150 | 5400 | 390 | 65.6 |
| Example 2 | B3 | 75 | A2 | 150 | 5400 | 410 | 66.4 |
| Example 3 | B4 | 75 | A2 | 150 | 5400 | 400 | 67.7 |
| Example 4 | B5 | 75 | A2 | 150 | 5400 | 410 | 66.6 |
| Example 5 | B6 | 75 | A2 | 150 | 5400 | 410 | 66.5 |
| Example 6 | B7 | 75 | A2 | 150 | 5400 | 400 | 66.9 |
| Example 7 | B8 | 75 | A2 | 150 | 5400 | 410 | 66.4 |
| Example 8 | B9 | 75 | A2 | 150 | 5400 | 400 | 67.1 |
| Example 9 | B10 | 75 | A2 | 150 | 5400 | 410 | 67.2 |
| Example 10 | B11 | 75 | A2 | 150 | 5400 | 410 | 68.2 |
| Example 11 | B12 | 75 | A2 | 150 | 5400 | 400 | 67.9 |
| Example 12 | B13 | 75 | A2 | 150 | 5400 | 400 | 68.4 |
| Example 13 | B14 | 75 | A2 | 150 | 5400 | 400 | 67.5 |
| Example 14 | B15 | 75 | A2 | 150 | 5400 | 410 | 68.2 |
| Example 15 | B16 | 75 | A2 | 150 | 5400 | 400 | 68.6 |
| Example 16 | B17 | 75 | A2 | 150 | 5400 | 390 | 68.3 |
| Example 17 | B18 | 75 | A2 | 150 | 5400 | 410 | 68.7 |
| Example 18 | B19 | 75 | A2 | 150 | 5400 | 390 | 68.0 |
| Example 19 | B20 | 75 | A2 | 150 | 5400 | 400 | 68.6 |
| Example 20 | B21 | 75 | A2 | 150 | 5400 | 390 | 68.4 |

TABLE 4-continued

|  | Reaction gas inlet side | | Reaction gas outlet side | | Space velocity hr$^{-1}$ | Reaction temperature °C. | PMDA Yield mol % |
| --- | --- | --- | --- | --- | --- | --- | --- |
|  | Catalyst | Layer length mm | Catalyst | Layer length mm |  |  |  |
| Example 21 | B22 | 75 | A2 | 150 | 5400 | 400 | 68.9 |
| Example 22 | B23 | 75 | A2 | 150 | 5400 | 400 | 69.0 |
| Example 23 | B24 | 75 | A2 | 150 | 5400 | 410 | 68.5 |
| Example 24 | B25 | 75 | A2 | 150 | 5400 | 400 | 68.8 |
| Example 25 | B26 | 75 | A2 | 150 | 5400 | 410 | 68.6 |
| Example 26 | B27 | 75 | A2 | 150 | 5400 | 400 | 67.9 |

TABLE 5

|  | Gas inlet side layer | | Intermediate layer | | Gas outlet side layer | | Space velocity hr$^{-1}$ | Reaction temperature °C. | PMDA Yield mol % |
| --- | --- | --- | --- | --- | --- | --- | --- | --- | --- |
|  | Catalyst | Layer Length mm | Catalyst | Layer length mm | Catalyst | Layer length mm |  |  |  |
| Example 27 | C1 | 50 | B12 | 75 | A1 | 150 | 4400 | 390 | 69.2 |
| Example 28 | C2 | 50 | B19 | 75 | A1 | 150 | 4400 | 380 | 69.4 |

As shown in the examples described above, high purity pyromellitic dianhydride can be produced at a high yield according to the present invention, and therefore not only the productivity is elevated but also the optimum reaction temperature is reduced, so that the operation can stably be carried out.

What is claimed is:

1. A process for producing pyromellitic dianhydride by feeding raw material mixed gas containing 1,2,4,5-tetraalkylbenzene and molecular oxygen to a fixed bed multitubular type reactor charged with a catalyst layer to carry out catalytic vapor phase oxidation, wherein the catalyst layer is divided into at least two layers of a layer at an outlet side of reaction gas and a layer at an inlet side of raw material mixed gas; and the layer at an outlet side of reaction gas is charged with a catalyst A represented by the following formula (1):

$$V_a(A)_b P_c Ag_d(B)_e O_x \qquad (1)$$

wherein V represents vanadium; P represents phosphorus; Ag represents silver; (A) represents at least one element selected from molybdenum and tungsten; (B) represents at least one element selected from alkaline metals and alkaline earth metals; O represents an oxygen element; a, b, c, d, e and x each represent an atomic number thereof, and when a is 1, 0<b≦2, 0<c≦1, d=0 to 0.2 and e=0 to 0.1, and x is a value determined by oxidation states of the respective elements other than an oxygen element, and the layer at an inlet side of raw material mixed gas is charged with a catalyst B represented by the following formula (2):

$$V_a Ti_b(C)_c(D)_d Ce_e O_x \qquad (2)$$

wherein V represents vanadium; Ti represents titanium; Ce represents cerium; (C) represents at least one element selected from rare earth elements (excluding cerium); (D) represents at least one element selected from phosphorus, antimony, hafnium, niobium, tantalum, boron and sulfur; O represents an oxygen element; a, b, c, d, e and x each represent an atomic number thereof, and when a is 1, 0<b≦500, 0<c≦0.5, d=0 to 1 and e=0 to 0.5, and x is a value determined by oxidation states of the respective elements other than an oxygen element.

2. The process as described in claim 1, wherein a layer of an inactive material selected from silica, alumina, steatite, cordierite, silicon carbide and metal Raschig rings is provided in the middle between the catalyst A layer and the catalyst B layer.

3. A process for producing pyromellitic dianhydride by feeding raw material mixed gas containing 1,2,4,5-tetraalkylbenzene and molecular oxygen to a fixed bed multitubular type reactor charged with a catalyst layer to carry out catalytic vapor phase oxidation, wherein the catalyst layer is divided into at least three layers of a layer at an outlet side of reaction gas, an intermediate layer and a layer at an inlet side of raw material mixed gas; the layer at an outlet side of reaction gas is charged with a catalyst A represented by the following formula (1):

$$V_a(A)_b P_c Ag_d(B)_e O_x \qquad (1)$$

wherein V represents vanadium; P represents phosphorus; Ag represents silver; (A) represents at least one element selected from molybdenum and tungsten; (B) represents at least one element selected from alkaline metals and alkaline earth metals; O represents an oxygen element; a, b, c, d, e and x each represent an atomic number thereof, and when a is 1, 0<b≦2, 0<c≦1, d=0 to 0.2 and e=0 to 0.1, and x is a value determined by oxidation states of the respective elements other than an oxygen element; the intermediate layer is charged with a catalyst B represented by the following formula (2):

$$V_a Ti_b(C)_c(D)_d Ce_e O_x \qquad (2)$$

wherein V represents vanadium; Ti represents titanium; Ce represents cerium; (C) represents at least one element selected from rare earth elements (excluding cerium); (D) represents at least one element selected from phosphorus, antimony, hafnium, niobium, tantalum, boron and sulfur; O represents an oxygen element; a, b, c, d, e and x each represent an atomic number thereof, and when a is 1, 0<b≦500, 0<c≦0.5, d=0 to 1 and e=0 to 0.5, and x is a value determined by oxidation states of the respective elements other than an oxygen element; and the layer at an inlet side of raw material mixed gas at an inlet side of raw material mixed gas is charged with a catalyst C represented by the following formula (3):

$$V_a(E)_b(F)_c(G)_d O_x \qquad (3)$$

wherein V represents vanadium; (E) represents at least one element selected from alkaline metals; (F) represents at least one element selected from phosphorus and copper; (G) represents at least one element selected from silver, sulfur, tantalum, boron, tungusten, and molybdenum; O represents an oxygen element; a, b, c, d and x each represent an atomic number thereof, and when a is 1, $0<b\leqq 2.5$, c=0 to 3 and d=0–2, and x is a value determined by oxidation states of the respective elements other than an oxygen element.

4. The process as described in claim 3, wherein a layer of an inactive material selected from silica, alumina, steatite, cordierite, silicon carbide and metal Raschig rings is provided in the middle between the catalyst A layer and the catalyst B layer and/or the middle between the catalyst B layer and the catalyst C layer.

5. A process for producing pyromellitic dianhydride by feeding raw material mixed gas containing 1,2,4,5-tetramethylbenzene and molecular oxygen to a fixed bed multitubular type reactor charged with a catalyst layer to carry out catalytic vapor phase oxidation, wherein the catalyst layer is divided into at least two layers of a layer at an outlet side of reaction gas and a layer at an inlet side of raw material mixed gas; and the layer at an outlet side of reaction gas is charged with a catalyst A represented by the following formula (1):

$$V_a(A)_b P_c Ag_d(B)_e O_x \qquad (1)$$

wherein V represents vanadium; P represents phosphorus; Ag represents silver; (A) represents molybdenum; (B) represents calcium; O represents an oxygen element; a, b, c, d, e and x each represent an atomic number thereof, and when a is 1, $0<b\leqq 2$, c=0.01 to 1.0, d=2 or less and e=0.01 or less, and x is a value determined by oxidation states of the respective elements other than an oxygen element, and the layer at an inlet side of raw material mixed gas is charged with a catalyst B represented by the following formula (2):

$$V_a Ti_b(C)_c(D)_d Ce_e O_x \qquad (2)$$

wherein V represents vanadium; Ti represents titanium; Ce represents cerium; (C) represents at least one element selected from rare earth elements (excluding cerium); (D) represents at least one element selected from phosphorus and antimony, O represents an oxygen element; a, b, c, d, e and x each represent an atomic number thereof, and when a is 1, b=2 to 50, c=0.001 to 0.2, d=1 or less, and e=0 to 0.5, and x is a value determined by oxidation states of the respective elements other than an oxygen element.

6. The process as described in claim 5, wherein a layer of an inactive material selected from silica, alumina, steatite, cordierite, silicon carbide and metal Raschig rings is provided in the middle between the catalyst A layer and the catalyst B layer.

7. A process for producing pyromellitic dianhydride by feeding raw material mixed gas containing 1,2,4,5-tetramethylbenzene and molecular oxygen to a fixed bed multitubular type reactor charged with a catalyst layer to carry out catalytic vapor phase oxidation, wherein the catalyst layer is divided into at least three layers of a layer at an outlet side of reaction gas, an intermediate layer and a layer at an inlet side of raw material mixed gas; the layer at an outlet side of reaction gas is charged with a catalyst A represented by the following formula (1):

$$V_a(A)_b P_c Ag_d(B)_e O_x \qquad (1)$$

wherein V represents vanadium; P represents phosphorus; Ag represents silver; (A) represents molybdenum; (B) represents calcium; O represents an oxygen element; a, b, c, d, e and x each represent an atomic number thereof, and when a is 1, $0<b\leqq 2$, c=0.01 to 1.0, d=2 or less and e=0.01 or less, and x is a value determined by oxidation states of the respective elements other than an oxygen element;

the intermediate layer is charged with a catalyst B represented by the following formula (2):

$$V_a Ti_b(C)_c(D)_d Ce_e O_x \qquad (2)$$

wherein V represents vanadium; Ti represents titanium; Ce represents cerium; (C) represents at least one element selected from rare earth elements (excluding cerium); (D) represents at least one element selected from phosphorus and antimony; O represents an oxygen element; a, b, c, d, e and x each represent an atomic number thereof and when a is 1, b=2 to 50, c=0.001 to 0.2, d=1 or less and e=0 to 0.5, and x is a value determined by oxidation states of the respective elements other than an oxygen element; and the layer at an inlet side of raw material mixed gas at an inlet side of raw material mixed gas is charged with a catalyst C represented by the following formula (3):

$$V_a(E)_b(F)_c(G)_d O_x \qquad (3)$$

wherein V represents vanadium; (E) represents at least one element selected from potassium and cesium; (F) represents at least one element selected from phosphorus and copper; (G) represents at least one element selected from sulfur, tungsten, and molybdenum; O represents an oxygen element; a, b, c, d, and x each represent an atomic number thereof, and when a is 1, b=0.2 to 2, c=0.2 to 2.5 and d=0–2, and x is a value determined by oxidation states of the respective elements other than an oxygen element.

8. The process as described in claim 7, wherein a layer of an inactive material selected from silica, alumina, steatite, cordierite, silicon carbide and metal Raschig rings is provided in the middle between the catalyst A layer and the catalyst B layer and/or the middle between the catalyst B layer and the catalyst C layer.

* * * * *